US012709588B2

(12) United States Patent
Kishima et al.

(10) Patent No.: US 12,709,588 B2
(45) Date of Patent: Aug. 18, 2026

(54) INTERNAL OLEFIN PRODUCTION METHOD

(71) Applicant: KAO CORPORATION, Tokyo (JP)

(72) Inventors: Takahiro Kishima, Wakayama (JP); Shingo Takada, Wakayama (JP); Hidehito Ikebata, Wakayama (JP)

(73) Assignee: KAO CORPORATION, Tokyo (JP)

( * ) Notice: Subject to any disclaimer, the term of this patent is extended or adjusted under 35 U.S.C. 154(b) by 128 days.

(21) Appl. No.: 18/692,123

(22) PCT Filed: Sep. 16, 2022

(86) PCT No.: PCT/JP2022/034661
§ 371 (c)(1),
(2) Date: Mar. 14, 2024

(87) PCT Pub. No.: WO2023/042898
PCT Pub. Date: Mar. 23, 2023

(65) Prior Publication Data

US 2025/0136532 A1 May 1, 2025

(30) Foreign Application Priority Data

Sep. 17, 2021 (JP) ................................ 2021-152297

(51) Int. Cl.
*C07C 5/25* (2006.01)

(52) U.S. Cl.
CPC .......... *C07C 5/2518* (2013.01); *C07C 5/2512* (2013.01); *C07C 2521/04* (2013.01); *C07C 2529/06* (2013.01)

(58) Field of Classification Search
CPC . C07C 5/2518; C07C 5/2512; C07C 2521/04; C07C 2529/06; C07C 2529/70; C07C 11/02
See application file for complete search history.

(56) References Cited

U.S. PATENT DOCUMENTS 6,054,629 A * 4/2000 Baralt .................. C07C 5/2556
585/670
2006/0084831 A1 4/2006 Zhang
2010/0286458 A1 11/2010 Iselborn et al.

FOREIGN PATENT DOCUMENTS

EP 0 139 774 A1 5/1985
EP 1 136 122 A1 9/2001
EP 2 990 395 A1 3/2016
EP 3724156 B1 * 5/2023 ........... C07C 5/2518
JP 8-508750 A 9/1996
JP 2002-520378 A 7/2002
JP 2004-285000 A 10/2004
JP 2008-517062 A 5/2008
JP 2011-6711 A 1/2011
JP 2011-500628 A 1/2011
JP 2014-144945 A 8/2014
JP 2014-156462 A 8/2014
JP 2014-224107 A 12/2014
WO WO 94/24076 A1 10/1994

OTHER PUBLICATIONS

Lehman et al., Olefin isomerization promoted by olefin metathesis catalysts, 2003, Inorganica Chimica Acta, 345, 190-198 (Year: 2003).*
International Search Report for International Application No. PCT/JP2022/034661, dated Oct. 11, 2022, with English translation.
Extended European Search Report for European Application No. 22870045.6, dated Feb. 3, 2026.

* cited by examiner

*Primary Examiner* — Cephia D Toomer
(74) *Attorney, Agent, or Firm* — Birch, Stewart, Kolasch & Birch, LLP

(57) ABSTRACT

A method of producing an internal olefin, including the step 1 and the step 2 below in this order. Step 1: a step of isomerizing a raw material olefin having 8 or more and 36 or less carbon atoms to provide an internal olefin containing a 1-olefin Step 2: a step of isomerizing the 1-olefin contained in the internal olefin provided in the step 1 at a temperature that is lower than the reaction temperature in the step 1.

16 Claims, No Drawings

INTERNAL OLEFIN PRODUCTION METHOD

FIELD OF THE INVENTION

The present invention relates to a method of producing an internal olefin.

BACKGROUND OF THE INVENTION

Internal olefins have been widely used as a base oil for an oil drilling fluid, a raw material of a chemical product, and the like.

An internal olefin is produced from a 1-olefin or the like through double bond isomerization, metathesis reaction, or the like.

For example, JP 2008-517062 A (PTL 1) describes a method of isomerizing a 1-alken to an internal alkene, including:

(a) combining at least one kind of a 1-alkene and a catalyst in a liquid phase at a temperature of approximately 50° C. to approximately 200° C., in which the catalyst is formed by bringing (i) at least one kind of a Group 8 transition metal salt and (ii) at least one kind of an alkyl aluminum compound into contact with each other to provide a first mixture; and (b) combining the first mixture in the step (a) and at least one kind of acid-cleaned clay at a temperature of approximately 100° C. to approximately 300° C. to form a final mixture.

SUMMARY OF THE INVENTION

The present invention relates to a method of producing an internal olefin, including the step 1 and the step 2 below in this order.

Step 1: a step of isomerizing a raw material olefin having 8 or more and 36 or less carbon atoms to provide an internal olefin containing a 1-olefin Step 2: a step of isomerizing the 1-olefin contained in the internal olefin provided in the step 1 at a temperature that is lower than the reaction temperature in the step 1

DETAILED DESCRIPTION OF THE INVENTION

The isomerization method of an olefin described in PTL 1 considers the method of isomerizing an α-olefin (1-olefin) for providing a final product containing an internal alkene and a low level oligomer, and the amount of the remaining α-olefin is not considered therein.

The present invention relates to a method of producing an internal olefin having a decreased 1-olefin content while preventing the double bond distribution of the internal olefin from being changed.

The present inventors have found that an internal olefin having a decreased 1-olefin content can be obtained while preventing the double bond distribution of the internal olefin from being changed, in such a manner that a raw material olefin having a particular number of carbon atoms is isomerized to provide an internal olefin containing 1-olefin, which is then further internally isomerized at a lower reaction temperature.

The present invention relates to the following item [1].

[1] A method of producing an internal olefin, including a step 1 and a step 2 in this order:

step 1: a step of isomerizing a raw material olefin having 8 or more and 36 or less carbon atoms to provide an internal olefin containing a 1-olefin; and step 2: a step of isomerizing the 1-olefin contained in the internal olefin provided in the step 1 at a temperature that is lower than a reaction temperature in the step 1.

The present invention can provide a method of producing an internal olefin having a decreased 1-olefin content while preventing the double bond distribution of the internal olefin from being changed.

[Method of producing Internal Olefin]

The method of producing an internal olefin of the present invention includes the step 1 and the step 2 below in this order.

Step 1: a step of isomerizing a raw material olefin having 8 or more and 36 or less carbon atoms to provide an internal olefin containing a 1-olefin Step 2: a step of isomerizing the 1-olefin contained in the internal olefin provided in the step 1 at a temperature that is lower than the reaction temperature in the step 1

The production method of the present invention provides a method of producing an internal olefin having a decreased 1-olefin content while preventing the double bond distribution of the internal olefin from being changed.

The internal olefin is formed by isomerizing the raw material olefin, i.e., rearranging the double bond position. The isomerization (isomerization reaction) herein may be internal isomerization (internal isomerization reaction).

In general, an internal olefin has a distribution of the double bond position thereof. The properties, such as the fluidity, the melting point, and the clouding point, of an internal olefin varies depending on the distribution of the double bond position, and therefore the internal olefin has a suitable distribution of the double bond position corresponding to the purposes. The amount of a 1-olefin in an internal olefin largely influences the properties above. For example, WO 2019/118226 teaches that the decrease of the 1-olefin amount in the internal olefin from approximately 10% to approximately 3% can reduce the pour point from approximately −10° C. to −22° C. (in a system containing at least one kind of a C14-C24 olefin). Thus, a large 1-olefin amount in an internal olefin causes a tendency of deterioration in quality, for example, decrease in fluidity.

As described above, in the production of an internal olefin, it is important that the isomerization is performed until providing a double bond distribution corresponding the purpose, and simultaneously the content of a 1-olefin is decreased as much as possible.

The ordinary isomerization method as described in PTL 1 is difficult to isomerize the 1-olefin selectively. In the case where the 1-olefin content is decreased through isomerization, the rearrangement of internal double bonds simultaneously occurs, and therefore the double bond distribution is changed.

In the present invention, the use of the step 2 enables a method of decreasing the 1-olefin content while preventing the double bond distribution of the internal olefin from being changed.

In the present invention, in the case where a 1-olefin having 8 or more and 36 or less carbon atoms as a raw material is isomerized to provide an internal olefin, the reaction proceeds as follows.

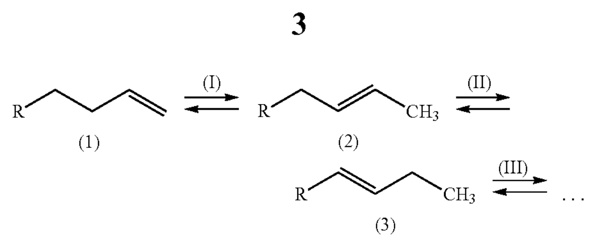

In the formula, R represents an alkyl group having 4 or more and 32 or less carbon atoms.

The 1-olefin having 8 or more carbon atoms (raw material olefin) (1) forms an internal olefin (2) through internal isomerization reaction represented by (I). The internal olefin (2) further forms an internal olefin (3) through rearrangement reaction of the double bond position (internal isomerization reaction) represented by (II). This isomerization of the double bond of the olefin proceeds through consecutive equilibrium reaction.

In the isomerization reaction (II) from the internal olefin (2) to the internal olefin (3), the equilibrium constant $K_{(2-3)}$ is approximately 1, and the equilibrium constants in the subsequent isomerization reaction (III) and following each are approximately 1. On the other hand, it has been found that there is a tendency that the lower the temperature is, the larger the equilibrium constant $K_{(1-2)}$ of the isomerization reaction (I) from the 1-olefin (1) to the 2-olefin (2) is. In other words, it is considered that the isomerization reaction from the 1-olefin (1) to the 2-olefin (2) advantageously proceeds at a lower temperature as compared to the subsequent isomerization reactions of the internal double bond.

In the present invention, after providing the internal olefin having the target average double bond position in the step 1, isomerization thereof is performed in the step 2 at a lower temperature than the reaction temperature (isomerization reaction temperature) in the step 1, and thereby it is estimated that the internal isomerization from the 1-olefin to the 2-olefin preferentially occurs in the step 2, and thus the internal olefin having a decreased 1-olefin content can be obtained while preventing the double bond distribution of the internal olefin from being changed.

The mechanism of the effects of the present invention described above is an estimation, and is not limited thereto.

In the following, the raw material olefin and the catalyst used in the present invention will be described, and then the steps 1 and 2 will be described in detail.

[Raw Material Olefin]

The raw material olefin is an olefin having 8 or more and 36 or less carbon atoms from the standpoint of the reactivity. The number of carbon atoms of the raw material olefin is preferably 8 or more, more preferably 10 or more, further preferably 12 or more, still further preferably 14 or more, and still more further preferably 16 or more, and is preferably 24 or less, more preferably 22 or less, further preferably 20 or less, and still further preferably 18 or less, from the standpoint of the usefulness of the resulting internal olefin.

Examples of the raw material olefin include octene, nonene, decene, undecene, dodecene, tridecene, tetradecene, pentadecene, hexadecene, heptadecene, octadecene, nonadecene, eicosene, heneicosene, docosene, tricosene, and tetracosene, and hexadecene and octadecene are preferred from the standpoint of the availability.

The double bond position of the raw material olefin is not particularly limited, and is preferably 1 or more and 4 or less, more preferably 1 or more and 3 or less, and further preferably 1 or 2, from the standpoint of the availability. Accordingly, the raw material olefin is preferably a 1-olefin, a 2-olefin, a 3-olefin, or a 4-olefin, more preferably a 1-olefin, a 2-olefin, or a 3-olefin, and further preferably a 1-olefin or a 2-olefin. The raw material olefin may be a mixture of two or more kinds of olefins having double bond positions different from each other.

The raw material olefin preferably contains at least a 1-olefin, and the 1-olefin is preferably a linear 1-olefin, from the standpoint of the availability.

The average double bond position of the raw material olefin is preferably 3.0 or less, more preferably 2.0 or less, and further preferably 1.8 or less, and is 1.0 or more, from the standpoint of the availability.

The raw material olefin may be obtained by any method, and the raw material olefin may be a commercially available olefin having 8 or more and 36 or less carbon atoms, preferably a commercially available 1-olefin having 8 or more and 36 or less carbon atoms, and may be produced through dehydration reaction of an aliphatic primary alcohol having 8 or more and 36 or less carbon atoms (a linear aliphatic primary alcohol having 8 or more and 36 or less carbon atoms) as a raw material (raw material alcohol). The reaction formula is as follows.

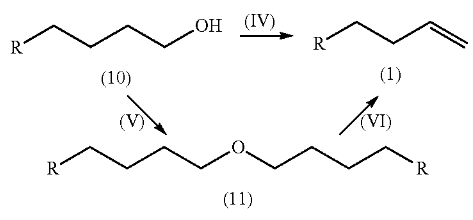

In the formula, R represents an alkyl group having 4 or more carbon atoms, and preferably represents a linear alkyl group having 4 or more carbon atoms from the standpoint of the usefulness.

The aliphatic primary alcohol (raw material alcohol) (10) forms the 1-olefin (1) through intramolecular dehydration represented by (IV), and simultaneously forms the 1-olefin (1) via a dialkyl ether (11) as a reaction intermediate through intermolecular dehydration represented by (V) and (VI). A part of the 1-olefin (1) thus formed becomes an internal olefin having a double bond position nearer the end thereof, such as a 2-olefin, through isomerization reaction.

The raw material alcohol may be any of an alcohol derived from petroleum and an alcohol derived from natural materials.

Examples of the aliphatic primary alcohol derived from natural materials include alcohols derived from a coconut oil, a palm oil, a palm kernel oil, a soybean oil, a rapeseed oil, beef tallow, lard, a tall oil, and a fish oil.

Examples of the aliphatic primary alcohol include n-butanol, n-pentanol, n-hexanol, n-heptanol, n-octanol, n-nonanol, n-decanol, n-undecanol, n-dodecanol, n-tridecanol, n-tetradecanol, n-pentadecanol, n-hexadecanol, n-heptadecanol, n-octadecanol, n-nonadecanol, n-eicosanol, n-heneicosanol, n-docosanol, n-tricosanol, and n-tetracosanol, and among these, n-hexadecanol and n-octadecanol are preferred.

The method of producing the raw material olefin from the raw material alcohol is not particularly limited, and the raw material olefin may be produced by any known production method, and is preferably produced through liquid phase dehydration reaction in the presence of a solid catalyst, preferably in the presence of a solid acid catalyst, in which the solid catalyst is preferably a metal oxide containing aluminum.

The reaction temperature of the liquid phase dehydration reaction is preferably 255° C. or more and 300° C. or less. The reaction pressure thereof is more preferably ordinary pressure.

[Catalyst]

In the present invention, the step 1 and the step 2 each are preferably performed in the presence of a catalyst from the standpoint of the reactivity of the isomerization reaction. The catalyst for the steps 1 and 2 preferably contains an element of the third to fifth periods, more preferably contains at least one selected from aluminum (Al), silicon (Si), titanium (Ti), iron (Fe), zinc (Zn), yttrium (Y), zirconium (Zr), and tin (Sn), and further preferably contains at least aluminum, from the standpoint of the reactivity of the isomerization reaction.

The catalyst is preferably a solid catalyst, and more preferably a solid acid catalyst, from the standpoint of the reactivity and the easiness in operation.

Specifically, the catalyst is preferably at least one kind selected from an aluminum oxide catalyst (which may be hereinafter referred simply to as “aluminum oxide”), an aluminum phosphate catalyst, and a zeolite (aluminosilicate) catalyst, and more preferably an aluminum oxide catalyst, from the standpoint of the reactivity and the reaction selectivity.

The “reactivity” herein means a high catalyst activity in the internal isomerization reaction, and the “reaction selectivity” herein means that reactions other than the internal isomerization reaction, such as a dimerization reaction, are unlikely to occur, but the internal isomerization reaction selectively occurs.

Examples of the crystal form of the aluminum oxide ($Al_2O_3$) include γ, δ, and θ, and the aluminum oxide is preferably γ-alumina from the standpoint of the achievement of a high catalyst activity.

The purity of aluminum oxide in the aluminum oxide catalyst is preferably 80% by mass or more, more preferably 90% by mass or more, further preferably 95% by mass or more, and still further preferably 98% by mass or more, from the standpoint of the reactivity and the reaction selectivity, and the upper limit thereof is not particularly limited, and is 100% by mass.

The average pore diameter of the catalyst is preferably 0.6 nm or more, more preferably 3 nm or more, and further preferably 6 nm or more, and is preferably 20 nm or less, more preferably 15 nm or less, and further preferably 12.3 nm or less, from the standpoint of the reactivity and the reaction selectivity.

The average pore diameter of the solid catalyst can be measured by the method described in the examples.

The pore volume of the catalyst is preferably 0.1 mL/g or more, more preferably 0.15 mL/g or more, further preferably 0.2 mL/g or more, and still further preferably 0.3 mL/g or more, and is preferably 2.0 mL/g or less, more preferably 1.8 mL/g or less, further preferably 1.6 mL/g or less, still further preferably 0.8 mL/g or less, and still more further preferably 0.6 mL/g or less, from the standpoint of the reactivity and the reaction selectivity.

The BET specific surface area of the catalyst is preferably is preferably 80 $m^2/g$ or more, more preferably 100 $m^2/g$ or more, and further preferably 120 $m^2/g$ or more, and is preferably 700 $m^2/g$ or less, more preferably 600 $m^2/g$ or less, further preferably 300 $m^2/g$ or less, still further preferably 280 $m^2/g$ or less, and still more further preferably 250 $m^2/g$ or less, from the standpoint of the reactivity and the reaction selectivity.

The pore volume and the BET specific surface area of the solid catalyst can be measured by the method described in the examples.

The catalyst may be produced by any method, and preferred examples of the method include a precipitation method, an impregnation method, a sol-gel method, an alkoxide method, and a pH swing method from the standpoint of the preparation of the catalyst having the desired properties for achieving a high catalyst activity.

Preferred examples of the preparation method of aluminum oxide as a preferred catalyst in the present embodiment include a precipitation method, a sol-gel method, an alkoxide method, and a pH swing method, and more preferred examples thereof include a pH swing method, from the same standpoint.

The resulting aluminum oxide is preferably baked, and the baking temperature is preferably 400° C. or more, more preferably 450° C. or more, and further preferably 480° C. or more, and is preferably 900° C. or less, more preferably 850° C. or less, and further preferably 800° C. or less, from the standpoint of achieving a high catalyst activity.

The baking time is preferably 1 hour or more, more preferably 2 hours or more, and further preferably 3 hours or more, and is preferably 10 hours or less, more preferably 7 hours or less, and further preferably 5 hours or less, from the standpoint of achieving a high catalyst activity.

The atmosphere of baking is not particularly limited, and the baking may be performed under an inert gas, an oxidative atmosphere, or a reductive atmosphere. The baking may be performed in a sealed environment or a gas flow environment. In the present invention, the atmosphere is preferably a gas flow environment of air or oxygen from the standpoint of the catalyst activity.

One example of the method of regulating the average pore diameter of the aluminum oxide catalyst is a pH swing method. The pH swing method is one kind of the precipitation method, and in the precipitation method using an aluminum salt and an inorganic base as raw materials, the precipitate is formed while adding aqueous solutions of the raw materials alternately to swing the pH.

For example, in the case where aluminum chloride and ammonia are used as raw materials, when an aqueous ammonia is gradually added continuously to an aluminum chloride aqueous solution, the pH rises and exceeds 9. Thereafter, when an aluminum chloride aqueous solution is gradually added continuously thereto, the pH falls and reaches less than 4.

By allowing the swing width of the pH to deviate from the range of pH 4 to 9, which is the precipitate forming pH range of aluminum, in this manner, the microcrystals of aluminum formed in the precipitate forming pH range of pH 4 to 9 are dissolved and used for crystal growth at the time when the pH falls within the precipitate forming pH range, and thus the crystal particle diameter can be gradually increased. The crystal particle diameter, the specific surface area, and the pore structure can be regulated by the temperature, the retention time, the raw material concentrations, the pH swing width, the number of swing, and the like, and consequently the crystal particle diameter, the diameter of the pores as the gaps among the crystal particles, the pore volume, the specific surface area, and the like after baking can be regulated.

The synthesis of aluminum oxide (alumina) by the pH swing method is described, for example, in literatures including JP 1-16773 B, JP 2-56283 B, JP 56-120508 B, JP 57-44605 B, JP 2003-292820 A, JP 56-115638 A, and Ceramics, vol. 33, No. 4, pp. 299-302 (1998), which are incorporated herein by reference.

In the present invention, for example, the catalyst obtained by the above procedure is in an aggregated state, and is preferably used after appropriately pulverizing to a powder form or a spherical form, after forming into a granular form, or after molding into a noodle form, a pellet form, or the like.

In the case where the catalyst is molded into a noodle form, a molded article in a noodle form is preferably formed through extrusion molding, and in the case where the catalyst is molded into a pellet form, a molded article in a pellet form is preferably formed through tableting. In the case where the catalyst is molded into a granular form, a noodle form, a pellet form, or the like, the catalyst may be produced in such a manner that the catalyst is kneaded with a small amount of a binder, and the resulting mixture is dried depending on necessity, and then molded, followed by baking.

Examples of the binder used herein include a polymer compound or an inorganic compound. Examples of the polymer compound include a cellulose-based resin, such as carboxymethyl cellulose and hydroxyethyl cellulose; a fluorine-based resin, such as polytetrafluoroethylene and polyvinylidene fluoride; a urethane resin; an epoxy resin; a polyester resin; a phenol resin; a melamine resin; a silicone resin; polycarbotitanium; and polytitanocarbosilane. Examples of the inorganic compound include an inorganic compound sol, such as silica and alumina. The binder is preferably a polymer compound from the standpoint of the productivity of the catalyst.

In the case where the solid catalyst is powder, the average particle diameter of the powder is preferably 1 μm or more, more preferably 3 μm or more, further preferably 5 μm or more, and still further preferably 8 μm or more, and is preferably 300 μm or less, more preferably 200 μm or less, further preferably 100 μm or less, and still further preferably 30 μm or less, from the standpoint of the reactivity.

The average particle diameter can be measured by the method described in the examples.

In the case where the solid catalyst is granules, the average particle diameter of the granules is preferably 0.2 mm or more, more preferably 0.4 mm or more, and further preferably 0.6 mm or more, and is preferably 2.0 mm or less, more preferably 1.3 mm or less, and further preferably 0.8 mm or less, from the standpoint of the easiness in recovering the catalyst and the standpoint of the reactivity.

In the case where the solid catalyst is granules, the average particle diameter of the granules can be measured in the following manner. After vibrating sieves of 2,000, 1,400, 1,000, 710, 500, 355, 250, 180, 125, 90, 63, and 45 μm defined in JIS Z8801-1 (established on May 20, 2000, finally revised on Nov. 20, 2006) for 5 minutes, the 50% average diameter is calculated for the undersieve mass distribution by the sieving method, and is designated as the average particle diameter. Specifically, sieves of 2,000, 1,400, 1,000, 710, 500, 355, 250, 180, 125, 90, 63, and 45 μm defined in JIS Z8801-1 (established on May 20, 2000, finally revised on Nov. 20, 2006) are stacked on a tray in the order from the sieve having a smaller mesh, 100 g of granules are added onto the uppermost sieve of 2,000 μm, the assembly is covered with a lid, and vibrated on a rolling and tapping sieve shaking machine (available from HEIKO Manufacturing, Ltd., tapping: 156 per minute, rolling: 290 per minute) for 5 minutes, then the mass of the granules remaining on each of the sieves and the tray is measured, and the mass proportion (%) of the granules on each of the sieves is calculated. The mass proportions of the granules are accumulated in the order from the sieve having a smaller mesh on the tray, and the particle diameter at which the accumulated value reaches 50% is designated as the average particle diameter.

In the case where the solid catalyst is in a noodle form, the average diameter thereof is preferably 0.3 mm or more, more preferably 0.5 mm or more, and further preferably 0.7 mm or more, and is preferably 2.5 mm or less, more preferably 2.3 mm or less, and further preferably 2.0 mm or less, from the standpoint of the catalyst strength and the reactivity.

In the case where the solid catalyst is in a noodle form, the average length thereof is preferably 8 mm or less, more preferably 6 mm or less, and further preferably 5 mm or less, and is preferably 2 mm or more, more preferably 3 mm or more, and further preferably 4 mm or more, from the standpoint of the homogeneity in packing and the standpoint of the catalyst strength.

The average diameter and the average length can be measured with a caliper.

In the case where the solid catalyst is in a pellet form, the average diameter and the average height thereof each are preferably 1.5 mm or more, more preferably 2.0 mm or more, and further preferably 2.5 mm or more, and is preferably 5.0 mm or less, more preferably 4.0 mm or less, and further preferably 3.0 mm or less, from the standpoint of the catalyst strength and the reactivity.

The average diameter and the average height can be measured with a caliper.

In the case where the solid catalyst is in a spherical form, the average diameter thereof is preferably 1.0 mm or more, more preferably 1.5 mm or more, and further preferably 2.0 mm or more, and is preferably 5.0 mm or less, more preferably 4.0 mm or less, and further preferably 3.0 mm or less, from the standpoint of easiness in recovering and the reactivity.

The average diameter can be measured with a caliper.

In the case where the catalyst is a solid acid catalyst, the acid amount of the solid acid catalyst is preferably 0.1 mmol/g or more, more preferably 0.15 mmol/g or more, and further preferably 0.2 mmol/g or more, and is preferably 1.5 mmol/g or less, more preferably 1.0 mmol/g or less, further preferably 0.9 mmol/g or less, still further preferably 0.85 mmol/g or less, and still more further preferably 0.8 mmol/g or less, from the standpoint of the reactivity and the reaction selectivity.

The acid amount of the solid acid catalyst can be measured by an ordinary method of measuring acid amount, such as an ammonia temperature-programmed desorption method ($NH_3$-TPD).

The measurement method used for $NH_3$-TPD may be a measurement method ordinarily practiced. For example, the TPD measurement is performed after performing a pretreatment, an $NH_3$ adsorption treatment, and a vacuum treatment under the following condition.

Pretreatment: heating to 200° C. over 20 minutes, and retained for 1 hour, in helium $NH_3$ adsorption treatment: adsorbing $NH_3$ at 50° C. and 2.7 kPa for 10 minutes Vacuum treatment: treating at 50° C. for 4 hours at vacuum degree of 2.7 kPa TPD measurement: under helium gas stream at 50 mL/min, heating to 600° C. at a heating rate of 5° C./min The crushing strength of the solid catalyst is preferably 1 daN or more, more preferably 1.5 daN or more, and further preferably 2 daN or more, and is preferably 11 daN or less, more preferably 10 daN or less, and further preferably 9 daN or less, from the standpoint of the catalyst strength.

The crushing strength can be measured, for example, by applying a compression force to the granulated or molded catalyst with a breaking test machine or the like. The crushing pressure in the description herein is shown by the force that starts to cause a crack in the catalyst in applying a compression force to the granulated or molded catalyst.

In the case where the reaction mode is a batch mode, the amount of the catalyst used is preferably 0.5 part by mass or more, more preferably 1 part by mass or more, and further preferably 2 parts by mass or more, and is preferably 50 parts by mass or less, more preferably 40 parts by mass or less, and further preferably 35 parts by mass or less, per 100 parts by mass of the raw material olefin, from the standpoint of the reactivity.

[Organic Solvent]

In the production method of the present invention, it is preferred to use substantially no organic solvent from the standpoint of the productivity. In the production method of the present invention, however, an organic solvent may be used depending on necessity. The organic solvent that can be used in the present invention is not particularly limited, as far as being a liquid at the reaction temperature, being compatible with the raw material olefin and the internal olefin as the product, and not inhibiting the reaction, and may be a mixture. It is preferred that after the reaction, the solvent can be isolated from the product through difference in boiling point.

The organic solvent that can be used in the present invention is preferably a hydrocarbon-based organic solvent, such as a saturated aliphatic hydrocarbon and an aromatic hydrocarbon.

The saturated aliphatic hydrocarbon may be either linear or branched.

Specific examples of the saturated aliphatic hydrocarbon include a compound having 10 or more and 35 or less carbon atoms, such as tridecane, hexadecane, octadecane, eicosane, docosane, triacontane, and squalane.

The saturated aliphatic hydrocarbon may be a mixture, such as liquid paraffin, a naphthene-based hydrocarbon, and an isoparaffin-based hydrocarbon. A material that is solid at ordinary temperature and is liquid at the reaction temperature, such as solid paraffin, may also be used.

The saturated aliphatic hydrocarbon used may be an oligomer of propylene, isobutene, and the like.

Specific examples of the aromatic hydrocarbon include an alkylbenzene and an alkylnaphthalene, such as n-dodecylbenzene, n-tridecylbenzene, n-tetradecylbenzene, n-pentadecylbenzene, n-hexadecylbenzene, and diisopropylnaphthalene.

[Step 1]

The step 1 is a step of isomerizing the raw material olefin having 8 or more and 36 or less carbon atoms to provide an internal olefin containing a 1-olefin. In the present invention, the isomerization (isomerization reaction) in the step 1 preferably includes internal isomerization reaction as a primary reaction, and may include isomerization reaction where a 2-olefin becomes a 1-olefin, and the like.

(Reaction Mode)

The reaction system in the step 1 is not particularly limited, may be any of a heterogeneous system and a homogeneous system, and is preferably a heterogeneous system from the standpoint of efficiently recovering the internal olefin containing a 1-olefin formed.

In the method of producing an internal olefin, the reaction mode is not particularly limited, and may be appropriately selected from a batch mode and a continuous mode.

In the case where the reaction mode is a continuous mode, any of a fixed bed system and a suspended bed system may be used. Among these, a fixed bed system is preferably used from the standpoint of the easiness in operation.

(Reaction Temperature)

A liquid phase reaction is preferably used from the standpoint of the reactivity and the standpoint of the reaction selectivity, and the reaction temperature is preferably 100° C. or more, more preferably 120° C. or more, and further preferably 140° C. or more, from the same standpoints, and is preferably 400° C. or less, more preferably 350° C. or less, and further preferably 300° C. or less, from the same standpoints.

In the case where the catalyst is an aluminum oxide catalyst, the reaction temperature is preferably 120° C. or more, more preferably 140° C. or more, further preferably 160° C. or more, still further preferably 180° C. or more, and still more further preferably 200° C. or more, from the standpoint of the reactivity and the standpoint of the reaction selectivity, and is preferably 400° C. or less, more preferably 350° C. or less, and further preferably 300° C. or less, from the same standpoints.

In the case where the catalyst is a zeolite catalyst, the reaction temperature is preferably 100° C. or more, and more preferably 120° C. or more, from the standpoint of the reactivity and the standpoint of the reaction selectivity, and is preferably 400° C. or less, more preferably 350° C. or less, further preferably 300° C. or less, still further preferably 250° C. or less, still more further preferably 200° C. or less, and even further preferably 160° C. or less, from the same standpoints.

In the case where the reaction temperature ($T_1$) in the step 1 is fluctuated, the reaction temperature ($T_1$) may be an average value.

In the step 1, the reaction temperature ($T_1$) in the step 1 is preferably retained to a constant temperature from the standpoint of the stable production. Accordingly, the fluctuation range of the reaction temperature ($T_1$) in the step 1 is preferably in a certain range.

The fluctuation range of the reaction temperature ($T_1$) in the step 1 is preferably 10° C. or less, more preferably 5° C. or less, further preferably 3° C. or less, and still further preferably 1° C. or less, from the standpoint of the stable production. The fluctuation range may be 0° C. or more, or may exceed 0° C.

(Reaction Pressure)

The pressure in the reaction vessel in the reaction is not particularly limited, and in terms of absolute pressure, is preferably 1 MPa or less, more preferably 0.5 MPa or less, and further preferably 0.1 MPa or less, i.e., the atmospheric pressure, from the standpoint of the easiness in reaction operation.

(Reaction Atmosphere)

In the reaction, an inert gas may be introduced to the reaction vessel.

Examples of the inert gas include nitrogen, argon, and helium, and nitrogen is preferred from the standpoint of the availability.

(Reaction Time)

In the case where the reaction mode is a batch mode, the reaction time is preferably 0.25 hr or more, more preferably 0.5 hr or more, and further preferably 1.0 hr or more, and is preferably 20 hr or less, more preferably 16 hr or less, further preferably 12 hr or less, still further preferably 8 hr or less, and still more further preferably 5 hr or less, from the standpoint of the reactivity and the standpoint of preventing side reactions.

(Rotation Number of Agitation)

In the case where the reaction mode is a batch mode, the system is preferably agitated in the reaction for retaining the system homogeneously, and the rotation number of agitation in the reaction is preferably 800 rpm or less, more preferably 700 rpm or less, and further preferably 600 rpm or less, from the standpoint of the easiness in reaction operation, while depending on the scale of the reaction. The rotation number of agitation is preferably 10 rpm or more, more preferably 50 rpm or more, and further preferably 200 rpm or more, from the standpoint of the reaction efficiency.

(LHSV (Liquid Hourly Space Velocity))

In the case where the reaction mode is a continuous mode, the LHSV (liquid hourly space velocity) in the reaction is preferably 0.05 $hr^{-1}$ or more, more preferably 0.1 $hr^{-1}$ or more, further preferably 0.15 $hr^{-1}$ or more, still further preferably 0.5 $hr^{-1}$ or more, still more further preferably 1.0 $hr^{-1}$ or more, and even further preferably 2.0 $hr^{-1}$ or more, and is preferably 5.0 $hr^{-1}$ or less, and more preferably 3.0 $hr^{-1}$ or less, from the standpoint of the reaction efficiency.

(Average Double Bond Position of Internal Olefin)

The average double bond position of the internal olefin after completing the reaction in the step 1 is preferably deeper (more inner) than the average double bond position of the raw material olefin.

The average double bond position of the internal olefin after completing the reaction may be deeper (more inner) than the raw material olefin, and is preferably 1.5 or more, more preferably 2.0 or more, further preferably 2.5 or more, still further preferably 3.0 or more, and still more further preferably 3.3 or more, and is preferably 8.0 or less, more preferably 6.0 or less, further preferably 5.5 or less, still further preferably 5.0 or less, and still more further preferably 4.6 or less, from the standpoint of the usefulness of the internal olefin.

(Isolation of Internal Olefin)

The internal olefin obtained in the step 1 can be obtained by isolating the reaction product and the catalyst.

The internal olefin obtained in the step 1 in the description herein (which may also be referred to as a "reaction product") means the reaction product after subjecting the raw material olefin to isomerization reaction, contains at last a 1-olefin and an internal olefin, and may also contain a branched olefin, a dimerized olefin, and the like as side reaction products.

(Content of 1-Olefin)

The content of the 1-olefin in the internal olefin containing the 1-olefin obtained in the step 1 is preferably 20 parts by mol or less, more preferably 15 parts by mol or less, further preferably 12 parts by mol or less, still further preferably 10 parts by mol or less, still more further preferably 5 parts by mol or less, and even further preferably 3 parts by mol or less, per 100 parts by mol in total of the 1-olefin and the internal olefin, from the standpoint of the usefulness. The lower limit thereof is not particularly limited, may be more than 0 part by mol, and is preferably 0.5 part by mol or more, and more preferably 1.0 part by mol or more, from the standpoint of the easiness in production.

[Step 2]

The step 2 is a step of isomerizing the 1-olefin contained in the internal olefin provided in the step 1 at a temperature that is lower than the reaction temperature in the step 1. The isomerization (isomerization reaction) may be internal isomerization (internal isomerization reaction).

(Isomerization Reaction Mode)

The reaction system in the step 2 is not particularly limited, may be any of a heterogeneous system and a homogeneous system, and is preferably a heterogeneous system from the standpoint of efficiently recovering the internal olefin formed.

In the method of producing an internal olefin, the reaction mode is not particularly limited, and may be appropriately selected from a batch mode and a continuous mode.

In the case where the reaction mode is a continuous mode, any of a fixed bed system and a suspended bed system may be used. Among these, a fixed bed system is preferably used from the standpoint of the easiness in operation.

In the case where the step 1 is performed by a batch mode, the step 1 and the step 2 may be performed in the same reaction vessel.

(Reaction Temperature)

The reaction is performed at a temperature that is lower than the step 1 from the standpoint of decreasing the 1-olefin and the standpoint of preventing the average double bond position from being changed.

The reaction temperature in the step 2 is preferably a temperature that is lower than the reaction temperature in the step 1 by 30° C. or more, more preferably a temperature that is lower by 35° C. or more, further preferably a temperature that is lower by 50° C. or more, and still further preferably a temperature that is lower by 80° C. or more, from the standpoint of decreasing the 1-olefin and the standpoint of preventing the average double bond position from being changed. Accordingly, assuming that the reaction temperature in the step 1 is shown by $T_1$ (° C.), and the reaction temperature in the step 2 is shown by $T_2$ (° C.), $T_1$-$T_2$ (which may be hereinafter referred to as $\Delta T$) is preferably 30° C. or more, more preferably 35° C. or more, further preferably 50° C. or more, and still further preferably 80° C. or more, and is preferably 240° C. or less, more preferably 200° C. or less, and further preferably 150° C. or less.

The reaction temperature ($T_2$) in the step 2 can be appropriately determined to make $\Delta T$ falling within the aforementioned range in relation to the reaction temperature ($T_1$) in the step 1, and the reaction temperature $T_2$ is preferably 30° C. or more, and more preferably 40° C. or more, and is preferably 350° C. or less, more preferably 300° C. or less, further preferably 250° C. or less, and still further preferably 225° C. or less, from the standpoint of decreasing the 1-olefin and the standpoint of preventing the average double bond position from being changed.

In the case where the catalyst is an aluminum oxide catalyst, the reaction temperature $T_2$ is preferably 30° C. or more, more preferably 40° C. or more, further preferably 60° C. or more, still further preferably 80° C. or more, and still more further preferably 120° C. or more, and is preferably 350° C. or less, more preferably 300° C. or less, further preferably 250° C. or less, and still further preferably 225° C. or less, from the standpoint of decreasing the 1-olefin and the standpoint of preventing the average double bond position from being changed.

In the case where the catalyst is a zeolite catalyst, the reaction temperature $T_2$ is preferably 30° C. or more, and more preferably 40° C. or more, and is preferably 350° C. or less, more preferably 300° C. or less, further preferably 250° C. or less, still further preferably 225° C. or less, still more further preferably 200° C. or less, even further preferably 150° C. or less, even still further preferably 100° C. or less, and even still more further preferably 60° C. or less, from the same standpoints.

In the case where the reaction temperature ($T_2$) in the step 2 is fluctuated, the reaction temperature ($T_2$) may be an average value. ΔT may be the difference between the average values of the reaction temperature ($T_1$) and the reaction temperature ($T_2$).

The reaction temperature ($T_2$) in the step 2 is preferably retained to a constant temperature from the standpoint of decreasing the 1-olefin. Accordingly, the fluctuation range of the reaction temperature ($T_2$) in the step 2 is preferably in a certain range.

The fluctuation range of the reaction temperature ($T_2$) in the step 2 is preferably 50° C. or less, more preferably 40° C. or less, further preferably 30° C. or less, still further preferably 20° C. or less, still more further preferably 10° C. or less, even further preferably 5° C. or less, even still further preferably 3° C. or less, and even still more further preferably 1° C. or less, from the standpoint of decreasing the 1-olefin and the standpoint of preventing the average double bond position from being changed. The fluctuation range may be 0° C. or more, or may exceed 0° C.

(Reaction Pressure)

The pressure in the reaction vessel in the reaction is not particularly limited, and in terms of absolute pressure, is preferably 1 MPa or less, more preferably 0.5 MPa or less, and further preferably 0.1 MPa or less, i.e., the atmospheric pressure, from the standpoint of the easiness in reaction operation.

(Reaction Atmosphere)

In the reaction, an inert gas may be introduced to the reaction vessel.

Examples of the inert gas include nitrogen, argon, and helium, and nitrogen is preferred from the standpoint of the availability.

(Reaction Time)

In the case where the reaction mode is a batch mode, the reaction time is preferably 0.05 hr or more, more preferably 0.1 hr or more, further preferably 0.15 hr or more, still further preferably 0.25 hr or more, still more further preferably 0.5 hr or more, even further preferably 0.8 hr or more, even still further preferably 1.2 hr or more, and even still more further preferably 1.7 hr or more, and is preferably 60 hr or less, more preferably 50 hr or less, further preferably 45 hr or less, and still further preferably 40 hr or less, from the standpoint of decreasing the 1-olefin and the standpoint of preventing the average double bond position from being changed.

(Rotation Number of Agitation)

In the case where the reaction mode is a batch mode, the system is preferably agitated in the reaction for retaining the system homogeneously, and the rotation number of agitation in the reaction is preferably 800 rpm or less, more preferably 700 rpm or less, and further preferably 600 rpm or less, from the standpoint of the easiness in reaction operation, while depending on the scale of the reaction. The rotation number of agitation is preferably 20 rpm or more, more preferably 100 rpm or more, and further preferably 300 rpm or more, from the standpoint of the reaction efficiency.

(LHSV (Liquid Hourly Space Velocity))

In the case where the reaction mode is a continuous mode, the LHSV (liquid hourly space velocity) in the reaction is preferably 0.05 $hr^{-1}$ or more, more preferably 0.1 $hr^{-1}$ or more, and further preferably 0.15 $hr^{-1}$ or more, and is preferably 5.0 $hr^{-1}$ or less, more preferably 3.0 $hr^{-1}$ or less, further preferably 1.5 $hr^{-1}$ or less, still further preferably 0.7 $hr^{-1}$ or less, still more further preferably 0.5 $hr^{-1}$ or less, and even further preferably 0.3 $hr^{-1}$ or less, from the standpoint of decreasing the 1-olefin and the standpoint of the reaction efficiency.

(Change in Average Double Bond Position of Internal Olefin)

In the step 2, from the standpoint of decreasing the 1-olefin amount while preventing the average double bond position (ADBP) from being changed, assuming that the average double bond position of the internal olefin after completing the reaction in the step 2 is shown by $ADBP_2$, the average double bond position of the internal olefin after completing the reaction in the step 1 is shown by $ADBP_1$, and the absolute value of the difference between $ADBP_2$ and $ADBP_1$ ($|ADBP_2-ADBP_1|$) is shown by ΔADBP, ΔADBP is preferably 0.1 or less, more preferably 0.08 or less, further preferably 0.06 or less, still further preferably 0.04 or less, and still more further preferably 0.03 or less.

The lower limit thereof is not particularly limited, and is 0 or more.

The 1-olefin is internally isomerized in the step 2, and therefore in general $ADBP_2>ADBP_1$.

(Change in Content of 1-Olefin)

A larger value of the decrement value (Δ(1-Ole)) from the content (% by mol) of the 1-olefin in the 1-olefin and the internal olefin obtained in the step 1 to the content (% by mol) of the 1-olefin in the 1-olefin and the internal olefin obtained in the step 2 means that the 1-olefin amount is decreased in the step 2 and thus is preferred, and A (1-Ole) is preferably 0.1% by mol or more, and more preferably 0.2% by mol or more.

Δ(1-Ole) also depends on the content of the 1-olefin in the 1-olefin and the internal olefin obtained in the step 1.

(Isolation of Internal Olefin)

The internal olefin obtained in the step 2 can be obtained by isolating the reaction product and the catalyst.

The internal olefin obtained in the step 2 has a decreased 1-olefin content as compared to the content of the 1-olefin contained in the internal olefin obtained in the step 1, and also is prevented in change of the average double bond position.

[Applications of Internal Olefin]

The internal olefin is useful as a raw material or an intermediate raw material of a surfactant, an organic solvent, a fabric softener, a sizing agent, and the like, and is useful as a raw material of a surfactant.

An ionic compound can be produced by introducing an ionic group to the internal olefin obtained by the production method of the present invention. Specific examples thereof include the production of an internal olefin sulfonate salt through sulfonation of the resulting internal olefin.

The method of producing an internal olefin sulfonate salt preferably includes steps A to C below from the standpoint of the reactivity and the reaction selectivity.

Step A: a step of sulfonating an internal olefin produced by the method of producing an internal olefin of the present invention Step B: a step of neutralizing a sulfonated product obtained in the step A Step C: a step of hydrolyzing a neutralized product obtained in the step B The step A may also be the following step.

A step of producing an internal olefin by the method of producing an internal olefin of the present invention, and then sulfonating the internal olefin.

(Step A: Sulfonating Step)

The step A is a step of sulfonating the internal olefin produced by the method of producing an internal olefin of the present invention, and a sulfonated product is obtained in the step A.

The sulfonation reaction in the step A may be performed by reacting 1 mol of the internal olefin with preferably 1 mol or more and 1.2 mol or less of sulfur trioxide gas or sulfuric anhydride.

The reaction temperature in the sulfonation reaction is preferably 20° C. or more and 40° C. or less from the standpoint of the yield.

The sulfonation reaction can be performed by using liquid sulfuric anhydride instead of sulfur trioxide gas under condition of a reaction temperature of 0° C. or more and 10° C. or less.

(Step B: Neutralizing Step)

The step B is a step of neutralizing the sulfonated product obtained in the step A, and a neutralized product of the sulfonated product is obtained in the step B.

The neutralization in the step B may be performed by reacting an alkali aqueous solution containing an alkali in an amount of 1 time by mol or more and 1.5 times by mol or less of the theoretical value of the sulfonic acid group.

Preferred examples of the alkali aqueous solution used for the neutralization include a sodium hydroxide aqueous solution and a potassium hydroxide aqueous solution.

(Step C: Hydrolyzing Step)

The step C is a step of hydrolyzing the neutralized product obtained in the step B, and an olefin sulfonate salt is obtained in the step C.

The hydrolyzation in the step C may be performed in the presence of water at 90° C. or more and 200° C. or less for 30 minutes or more and 4 hours or less.

The resulting internal olefin sulfonate salt is useful as a surfactant.

In addition to the embodiments described above, the present invention discloses the following methods of producing an internal olefin.

<1> A method of producing an internal olefin, including a step 1 and a step 2 in this order:

step 1: a step of isomerizing a raw material olefin having 8 or more and 36 or less carbon atoms to provide an internal olefin containing a 1-olefin; and step 2: a step of isomerizing the 1-olefin contained in the internal olefin provided in the step 1 at a temperature that is lower than a reaction temperature in the step 1.

<2> The method of producing an internal olefin according to the item <1>, in which the reaction temperature in the step 1 is preferably 100° C. or more, more preferably 120° C. or more, and further preferably 140° C. or more, and is preferably 400° C. or less, more preferably 350° C. or less, and further preferably 300° C. or less.

<3> The method of producing an internal olefin according to the item <1>, in which the reaction temperature in the step 1 is 100° C. or more and 300° C. or less.

<4> The method of producing an internal olefin according to any one of the items <1> to <3>, in which the fluctuation range of the reaction temperature in the step 1 is preferably 10° C. or less, more preferably 5° C. or less, further preferably 3° C. or less, and still further preferably 1° C. or less, is 0° C. or more, or exceeds 0° C.

<5> The method of producing an internal olefin according to any one of the items <1> to <4>, in which the pressure in the reaction vessel in the reaction of the step 1 in terms of absolute pressure is preferably 1 MPa or less, more preferably 0.5 MPa or less, and further preferably 0.1 MPa or less, i.e., the atmospheric pressure.

<6> The method of producing an internal olefin according to any one of the items <1> to <5>, in which an inert gas is introduced to the reaction vessel in the reaction of the step 1.

<7> The method of producing an internal olefin according to the item <6>, in which the inert gas is preferably nitrogen, argon, or helium, and is more preferably nitrogen.

<8> The method of producing an internal olefin according to any one of the items <1> to <7>, in which the reaction mode of the step 1 is a batch mode.

<9> The method of producing an internal olefin according to the item <8>, in which the reaction time in the step 1 is preferably 0.25 hr or more, more preferably 0.5 hr or more, and further preferably 1.0 hr or more, and is preferably 20 hr or less, more preferably 16 hr or less, further preferably 12 hr or less, still further preferably 8 hr or less, and still more further preferably 5 hr or less.

<10> The method of producing an internal olefin according to the item <8> or <9>, in which agitation is performed in the reaction of the step 1.

<11> The method of producing an internal olefin according to the item <10>, in which the rotation number of agitation in the reaction of the step 1 is preferably 800 rpm or less, more preferably 700 rpm or less, and further preferably 600 rpm or less, and is preferably 10 rpm or more, more preferably 50 rpm or more, and further preferably 200 rpm or more.

<12> The method of producing an internal olefin according to any one of the items <1> to <7>, in which the reaction mode of the step 1 is a continuous mode.

<13> The method of producing an internal olefin according to the item <12>, in which the LHSV (liquid hourly space velocity) in the reaction of the step 1 is preferably 0.05 $hr^{-1}$ or more, more preferably 0.1 $hr^{-1}$ or more, further preferably 0.15 $hr^{-1}$ or more, still further preferably 0.5 $hr^{-1}$ or more, still more further preferably 1.0 $hr^{-1}$ or more, and even further preferably 2.0 $hr^{-1}$ or more, and is preferably 5.0 $hr^{-1}$ or less, and more preferably 3.0 $hr^{-1}$ or less.

<14> The method of producing an internal olefin according to any one of the items <1> to <13>, in which the reaction temperature in the step 2 is a temperature that is lower than the reaction temperature in the step 1 by 30° C. or more.

<15> The method of producing an internal olefin according to any one of the items <1> to <14>, in which the difference $T_1-T_2$ between the reaction temperature $T_1$ (° C.) in the step 1 and the reaction temperature $T_2$ (° C.) in the step 2 (which may be hereinafter referred to as $\Delta T$) is preferably 35° C. or more, more preferably 50° C. or more, and further preferably 80° C. or more, and is preferably 240° C. or less, more preferably 200° C. or less, and further preferably 150° C. or less.

<16> The method of producing an internal olefin according to any one of the items <1> to <15>, in which the reaction temperature $T_2$ in the step 2 is preferably 30° C. or more, and more preferably 40° C. or more, and is preferably 350° C. or less, more preferably 300° C. or less, further preferably 250° C. or less, and still further preferably 225° C. or less.

<17> The method of producing an internal olefin according to any one of the items <1> to <16>, in which the fluctuation range of the reaction temperature in the step 2 is preferably 50° C. or less, more preferably 40° C. or less, further preferably 30° C. or less, still further preferably 20° C. or less, still more further preferably 10° C. or less, even further preferably 5° C. or less, even still further preferably 3° C. or less, and even still more further preferably 1° C. or less, may be 0° C. or more, or may exceed 0° C.

<18> The method of producing an internal olefin according to any one of the items <1> to <17>, in which the number of carbon atoms of the raw material olefin is preferably 10 or more, more preferably 12 or more, further preferably 14 or more, and still further preferably 16 or more, and is preferably 24 or less, more preferably 22 or less, further preferably 20 or less, and still further preferably 18 or less.

<19> The method of producing an internal olefin according to any one of the items <1> to <18>, in which the raw material olefin contains a 1-olefin.

<20> The method of producing an internal olefin according to the item <19>, in which the 1-olefin is a linear 1-olefin.

<21> The method of producing an internal olefin according to any one of the items <1> to <20>, in which the step 1 and the step 2 each are performed in the presence of a catalyst.

<22> The method of producing an internal olefin according to the item <21>, in which the catalyst preferably contains an element of the third to fifth periods, more preferably contains at least one selected from aluminum (Al), silicon (Si), titanium (Ti), iron (Fe), zinc (Zn), yttrium (Y), zirconium (Zr), and tin (Sn), and further preferably contains at least aluminum.

<23> The method of producing an internal olefin according to the item <21> or <22>, in which the catalyst is a solid catalyst.

<24> The method of producing an internal olefin according to any one of the items <21> to <23>, in which the catalyst is a solid acid catalyst.

<25> The method of producing an internal olefin according to any one of the items <21> to <24>, in which the catalyst is an aluminum oxide catalyst.

<26> The method of producing an internal olefin according to the item <25>, in which the reaction temperature in the step 1 is preferably 120° C. or more, more preferably 140° C. or more, further preferably 160° C. or more, still further preferably 180° C. or more, and still more further preferably 200° C. or more, and is preferably 400° C. or less, more preferably 350° C. or less, and further preferably 300° C. or less.

<27> The method of producing an internal olefin according to the item <25> or <26>, in which the reaction temperature in the step 2 is preferably 30° C. or more, more preferably 40° C. or more, further preferably 60° C. or more, still further preferably 80° C. or more, and still more further preferably 120° C. or more, and is preferably 350° C. or less, more preferably 300° C. or less, further preferably 250° C. or less, and still further preferably 225° C. or less.

<28> The method of producing an internal olefin according to any one of the items <25> to <27>, in which the fluctuation range of the reaction temperature in the step 2 is preferably 50° C. or less, more preferably 40° C. or less, further preferably 30° C. or less, still further preferably 20° C. or less, still more further preferably 10° C. or less, even further preferably 5° C. or less, even still further preferably 3° C. or less, and even still more further preferably 1° C. or less, is 0° C. or more, or exceeds 0° C.

<29> The method of producing an internal olefin according to any one of the items <21> to <24>, in which the catalyst is a zeolite catalyst.

<30> The method of producing an internal olefin according to the item <29>, in which the reaction temperature in the step 1 is preferably 100° C. or more, and more preferably 120° C. or more, and is preferably 400° C. or less, more preferably 350° C. or less, further preferably 300° C. or less, still further preferably 250° C. or less, still more further preferably 200° C. or less, and even further preferably 160° C. or less.

<31> The method of producing an internal olefin according to the item <29> or <30>, in which the reaction temperature in the step 2 is preferably 30° C. or more, and more preferably 40° C. or more, and is preferably 350° C. or less, more preferably 300° C. or less, further preferably 250° C. or less, still further preferably 225° C. or less, still more further preferably 200° C. or less, even further preferably 150° C. or less, even still further preferably 100° C. or less, and even still more further preferably 60° C. or less.

<32> The method of producing an internal olefin according to any one of the items <29> to <31>, in which the fluctuation range of the reaction temperature in the step 2 is preferably 50° C. or less, more preferably 40° C. or less, further preferably 30° C. or less, still further preferably 20° C. or less, still more further preferably 10° C. or less, even further preferably 5° C. or less, even still further preferably 3° C. or less, and even still more further preferably 1° C. or less, is 0° C. or more, or exceeds 0° C.

<33> The method of producing an internal olefin according to any one of the items <1> to <32>, in which the absolute value of the difference between the average double bond position of the internal olefin obtained in the step 1 and the average double bond position of the internal olefin obtained in the step 2 is preferably 0.1 or less, more preferably 0.08 or less, further preferably 0.06 or less, still further preferably 0.04 or less, and still more further preferably 0.03 or less, and the lower limit thereof is not particularly limited, and is 0 or more.

<34> The method of producing an internal olefin according to any one of the items <1> to <33>, in which the average double bond position of the internal olefin after completing the reaction in the step 1 is more inner than the average double bond position of the raw material olefin.

<35> The method of producing an internal olefin according to any one of the items <1> to <34>, in which the average double bond position of the internal olefin after completing the reaction in the step 1 is preferably 1.5 or more, more preferably 2.0 or more, further preferably 2.5 or more, still further preferably 3.0 or more, and still more further preferably 3.3 or more, and is preferably 8.0 or less, more preferably 6.0 or less, further preferably 5.5 or less, still further preferably 5.0 or less, and still more further preferably 4.6 or less.

<36> The method of producing an internal olefin according to any one of the items <1> to <35>, in which the content of the 1-olefin in the internal olefin containing the 1-olefin obtained in the step 1 is preferably 20 parts by mol or less, more preferably 15 parts by mol or less, further preferably 12 parts by mol or less, still further preferably 10 parts by mol or less, still more further preferably 5 parts by mol or less, and even further preferably 3 parts by mol or less, may be more than 0 part by mol, and is preferably 0.5 part by mol or more, and more preferably 1.0 part by mol or more, per 100 parts by mol in total of the 1-olefin and the internal olefin.

<37> The method of producing an internal olefin according to any one of the items <1> to <36>, in which an inert gas is introduced to the reaction vessel in the reaction of the step 2.

<38> The method of producing an internal olefin according to the item <37>, in which the inert gas is preferably nitrogen, argon, or helium, and more preferably nitrogen.

<39> The method of producing an internal olefin according to any one of the items <1> to <38>, in which the reaction mode of the isomerization of the step 2 is a batch mode.

<40> The method of producing an internal olefin according to the item <39>, in which the reaction time in the step 2 is 0.05 hr or more and 60 hr or less.

<41> The method of producing an internal olefin according to the item <39> or <40>, in which the reaction time in the step 2 is preferably 0.05 hr or more, more preferably 0.1 hr or more, further preferably 0.15 hr or more, still further preferably 0.25 hr or more, still more further preferably 0.5 hr or more, even further preferably 0.8 hr or more, even still further preferably 1.2 hr or more, and even still more further preferably 1.7 hr or more, and is preferably 60 hr or less, more preferably 50 hr or less, further preferably 45 hr or less, and still further preferably 40 hr or less.

<42> The method of producing an internal olefin according to any one of the items <39> to <41>, in which agitation is performed in the reaction of the step 2.

<43> The method of producing an internal olefin according to the item <42>, in which the rotation number of agitation in the reaction of the step 2 is preferably 800 rpm or less, more preferably 700 rpm or less, and further preferably 600 rpm or less, and is preferably 20 rpm or more, more preferably 100 rpm or more, and further preferably 300 rpm or more.

<44> The method of producing an internal olefin according to any one of the items <1> to <38>, in which the reaction mode of the isomerization of the step 2 is a continuous mode.

<45> The method of producing an internal olefin according to the item <44>, in which the LHSV (liquid hourly space velocity) in the reaction of the step 2 is 0.05 $hr^{-1}$ or more and 5.0 $hr^{-1}$ or less.

<46> The method of producing an internal olefin according to the item <44> or <45>, in which the LHSV (liquid hourly space velocity) in the reaction of the step 2 is preferably 0.05 $hr^{-1}$ or more, more preferably 0.1 $hr^{-1}$ or more, and further preferably 0.15 $hr^{-1}$ or more, and is preferably 5.0 $hr^{-1}$ or less, more preferably 3.0 $hr^{-1}$ or less, further preferably 1.5 $hr^{-1}$ or less, still further preferably 0.7 $hr^{-1}$ or less, still more further preferably 0.5 $hr^{-1}$ or less, and even further preferably 0.3 $hr^{-1}$ or less.

<47> The method of producing an internal olefin according to any one of the items <1> to <46>, in which the decrement value from the content (% by mol) of the 1-olefin in the 1-olefin and the internal olefin obtained in the step 1 to the content (% by mol) of the 1-olefin in the 1-olefin and the internal olefin obtained in the step 2 is preferably 0.1% by mol or more, and more preferably 0.2% by mol or more.

<48> A method of producing an internal olefin sulfonate salt, including sulfonating an internal olefin produced by the method of producing an internal olefin according to any one of the items <1> to <47>.

<49> A method of producing an internal olefin sulfonate salt, including producing an internal olefin by the method of producing an internal olefin according to any one of the items <1> to <48>, and then sulfonating the internal olefin.

EXAMPLES

The present invention will be described specifically with reference to examples below, but the present invention is not limited to the examples. The property values were measured and evaluated in the following manner.

Example 1

[Step 1: Isomerization Reaction]

In a 3,000 mL four-neck flask, 1,562.6 g of 1-hexadecene (available from Fujifilm Wako Pure Chemical Corporation) as a raw material olefin and 78.1 g of γ-alumina ("GP-20", product name, γ-$Al_2O_3$, available from Mizusawa Industrial Chemicals, Ltd.) (5% by mass based on the raw material olefin) as a catalyst were charged and reacted at 260° C. under agitation at 500 rpm under a nitrogen stream in the system (nitrogen flow amount: 100 mL/min) for 2.6 hours. The fluctuation range of the reaction temperature in the step 1 herein was 1° C. or less. After cooling the reaction liquid to room temperature, the catalyst was filtered off to provide an internal olefin.

After completing the reaction, approximately two drops of the reaction liquid was collected and placed in a sample tube, to which 1 mL of dimethyldisulfide (available from Tokyo Kasei Kogyo Co., Ltd.) and 30 mg of iodine (available from Fujifilm Wako Pure Chemical Corporation) were added, which were sufficiently mixed and then allowed to stand at 65° C. for 15 minutes. Subsequently, 1 mL of a 30% by mass sodium thiosulfate aqueous solution (available from Fujifilm Wako Pure Chemical Corporation), 1 mL of ethanol (available from Fujifilm Wako Pure Chemical Corporation), and 2 mL of hexane were added thereto and mixed, and then the upper phase was collected and analyzed for quantitatively determining the products with a gas chromatography analyzer "Agilent 6890A" (available from Agilent Technologies, Inc.) equipped with a column "Ultra Alloy-1" (capillary column 30.0 m×250 μm, available from Frontier Laboratories Ltd.) and a hydrogen flame ionization detector (FID) under condition of an injection temperature of 300° C., a detector temperature of 350° C., and a He flow rate of 0.8 mL/min.

[Step 2]

In a 300 mL separable flask, 100.0 g of the internal olefin obtained in the step 1 and 5.0 g of γ-alumina ("GP-20", product name, γ-$Al_2O_3$, available from Mizusawa Industrial Chemicals, Ltd.) (5% by mass based on the olefin) as a catalyst were charged and reacted at 160° C. under agitation at 500 rpm with nitrogen flowing in the system (nitrogen flow amount: 100 mL/min) for 27 hours. The fluctuation range of the reaction temperature in the step 2 herein was 1° C. or less. After completing the reaction, the products were quantitatively determined in the same manner as in the step 1.

Examples 2 to 8 and Comparative Example 1

An internal olefin was obtained in the same manner as in Example 1 except that the kind and the amount of the catalyst used, the reaction temperature, the reaction time, and the raw material olefin were changed as shown in Table 1.

Zeolite used as a catalyst in Examples 4 and 7 was "CP814E", trade name, available from Zeolyst International, Inc.

1-Octadecene used as a raw material olefin in Example 8 was available from Fujifilm Wako Pure Chemical Corporation.

The properties of the catalysts used were measured in the following manner.

Specific surface area, pore diameter, pore volume: The specific surface area and pore diameter distribution were analyzed with ASAP 2020 (available from Shimadzu Corporation).

Acid amount: With Belcat (available from Nippon Bel Co., Ltd.), a specimen was heated to 500° C. at 10° C./min, and then retained at 500° C. for 1 hour, and NH; was then adsorbed with 5% $NH_3$—He at 100° C. The physically adsorbed $NH_3$ was removed by allowing He to flow at 100° C. for 15 minutes. $NH_3$ was desorbed by heating to 610° C. at 10° C./min, and the desorbed $NH_3$ was observed with TCD and MS.

The properties of GP-20 (available from Mizusawa Industrial Chemicals, Ltd., γ-$Al_2O_3$) were as follows.

Average particle diameter: 26 μm
BET specific surface area: 189 $m^2$/g
Average pore diameter: 12.1 nm
Pore volume: 0.50 mL/g
Acid amount: 0.28 mmol/g The properties of CP814E (available from Zeolyst International, Inc., zeolite) were as follows.

Average particle diameter: 9.9 μm
BET specific surface area: 656 $m^2$/g
Average pore diameter: <1 nm
Pore volume: >0.62 mL/g
Acid amount: 0.76 mmol/g

Example 9

[Step 1: Isomerization Reaction]

In a continuous catalyst evaluation device, 400 mL of a γ-alumina catalyst ("Neobead GB-13", product name, γ-$Al_2O_3$, available from Mizusawa Industrial Chemicals, Ltd., bead form, diameter: 2.0 mm, specific surface area: 180 $m^2$/g, average pore diameter: 11.1 nm, pore volume: 0.50 mL/g, acid amount: 0.28 mmol/g, crushing strength: 2.6 daN) as a catalyst was packed, to which 1-hexadecene (available from Fujifilm Wako Pure Chemical Corporation) as a raw material olefin was delivered at an LHSV of 2.9 $hr^{-1}$, and the continuous reaction was performed under a nitrogen stream at 27 NL/hr under condition of a pressure of 0.0 MPaG and a reaction temperature of 280° C. The fluctuation range of the reaction temperature in the step 1 herein was 1° C. or less. The reaction liquid was cooled and then recovered to provide an internal olefin. The products in the reaction liquid were quantitatively determined in the same manner as in Example 1.

[Step 2]

In a continuous catalyst evaluation device, 450 mL of a γ-alumina catalyst ("Neobead GB-13", product name, γ-$Al_2O_3$, available from Mizusawa Industrial Chemicals, Ltd., bead form, diameter: 2.0 mm, specific surface area: 180 $m^2$/g, average pore diameter: 11.1 nm, pore volume: 0.50 mL/g, acid amount: 0.28 mmol/g, crushing strength: 2.6 daN) as a catalyst was packed, to which the internal olefin obtained in the step 1 as a raw material olefin was delivered at an LHSV of 0.09 $hr^{-1}$, and the continuous reaction was performed under a nitrogen stream at 0.9 NL/hr under condition of a pressure of 0.1 MPaG and a reaction temperature of 160° C. The fluctuation range of the reaction temperature in the step 2 herein was 1° C. or less. The products in the reaction liquid were quantitatively determined in the same manner as in Example 1.

Example 10

[Step 1: Isomerization Reaction]

The isomerization reaction of an olefin was performed in the same manner as in the step 1 of Example 9.

[Step 2]

In a continuous catalyst evaluation device, 450 mL of a γ-alumina catalyst ("Neobead GB-13", product name, γ-$Al_2O_3$, available from Mizusawa Industrial Chemicals, Ltd., bead form, diameter: 2.0 mm, specific surface area: 180 $m^2$/g, average pore diameter: 11.1 nm, pore volume: 0.50 mL/g, acid amount: 0.28 mmol/g, crushing strength: 2.6 daN) as a catalyst was packed, to which the internal olefin obtained in the step 1 as a raw material olefin was delivered at an LHSV of 0.55 $hr^{-1}$, and the continuous reaction was performed under a nitrogen stream at 5.7 NL/hr under condition of a pressure of 0.1 MPaG and a reaction temperature of 160° C. The fluctuation range of the reaction temperature in the step 2 herein was 1° C. or less. The products in the reaction liquid were quantitatively determined in the same manner as in Example 1.

TABLE 1

| | | | Example 1 | Example 2 | Example 3 | Example 4 |
|---|---|---|---|---|---|---|
| | Number of carbon atoms | | 16 | 16 | 16 | 16 |
| Step 1 Condition | Raw material olefin | | 1-hexadecene | 1-hexadecene | 1-hexadecene | 1-hexadecene |
| | Catalyst | | γ-alumina | γ-alumina | γ-alumina | γ-alumina |
| | Temperature | [° C.] | 260 | 260 | 260 | 260 |
| | Time | [hr or min] | 2.6 hr | 2.6 hr | 2.6 hr | 2.6 hr |
| | LHSV | [$hr^{-1}$] | — | — | — | — |
| Step 2 Condition | Catalyst | | γ-alumina | γ-alumina | γ-alumina | zeolite |
| | Catalyst amount | wt % or mL | 5 wt % | 30 wt % | 2.5 wt % | 5 wt % |
| | Temperature | [° C.] | 160 | 130 | 220 | 50 |
| | Time | [hr or min] | 27 hr | 37 hr | 1.8 hr | 7 hr |
| | LHSV | [$hr^{-1}$] | — | — | — | — |
| Step 1 Composition after reaction | Composition [mol %] | 1-olefin | 2.7 | 2.7 | 2.7 | 2.7 |
| | | 2-olefin | 31.3 | 31.1 | 31.3 | 31.3 |
| | | 3-olefin | 24.3 | 24.2 | 24.3 | 24.2 |
| | | 4-olefin | 17.9 | 18.0 | 17.9 | 18.0 |
| | | 5-olefin | 10.5 | 10.6 | 10.5 | 10.5 |
| | | 6-olefin | 6.7 | 6.8 | 6.7 | 6.7 |
| | | 7-olefin | 3.3 | 3.3 | 3.3 | 3.3 |
| | | 8-olefin | 3.3 | 3.3 | 3.3 | 3.3 |
| | | 9-olefin | — | — | — | — |
| | | Total | 100.0 | 100.0 | 100.0 | 100.0 |
| | | $ADBP_1$ | 3.52 | 3.53 | 3.52 | 3.52 |

TABLE 1-continued

| | | | | | | |
|---|---|---|---|---|---|---|
| Step 2 Composition after reaction | Composition [mol %] | 1-olefin | 2.1 | 2.3 | 2.5 | 2.2 |
| | | 2-olefin | 31.2 | 31.3 | 30.9 | 31.4 |
| | | 3-olefin | 24.3 | 24.3 | 24.0 | 24.0 |
| | | 4-olefin | 18.2 | 18.0 | 18.2 | 18.1 |
| | | 5-olefin | 10.7 | 10.6 | 10.8 | 10.8 |
| | | 6-olefin | 6.8 | 6.8 | 6.8 | 6.9 |
| | | 7-olefin | 3.4 | 3.3 | 3.3 | 3.3 |
| | | 8-olefin | 3.4 | 3.3 | 3.3 | 3.3 |
| | | 9-olefin | — | — | — | — |
| | | Total | 100.0 | 100.0 | 100.0 | 100.0 |
| | | $ADBP_2$ | 3.55 | 3.53 | 3.55 | 3.54 |
| | Δ(1-Ole) | | 0.6 | 0.4 | 0.2 | 0.5 |
| | ΔADBP | | 0.03 | 0.00 | 0.03 | 0.02 |

| | | | Example 5 | Example 6 | Example 7 | Example 8 |
|---|---|---|---|---|---|---|
| | Number of carbon atoms | | 16 | 16 | 16 | 18 |
| Step 1 Condition | Raw material olefin | | 1-hexadecene | 1-hexadecene | 1-hexadecene | 1-octadecene |
| | Catalyst | | γ-alumina | γ-alumina | zeolite | γ-alumina |
| | Temperature | [° C.] | 260 | 260 | 150 | 220 |
| | Time | [hr or min] | 40 min | 8.5 hr | 50 min | 10 hr |
| | LHSV | [$hr^{-1}$] | — | — | — | — |
| Step 2 Condition | Catalyst | | γ-alumina | γ-alumina | zeolite | γ-alumina |
| | Catalyst amount | wt % or mL | 30 wt % | 30 wt % | 5 wt % | 5 wt % |
| | Temperature | [° C.] | 130 | 130 | 50 | 160 |
| | Time | [hr or min] | 37 hr | 37 hr | 7 hr | 16 hr |
| | LHSV | [$hr^{-1}$] | — | — | — | — |
| Step 1 Composition after reaction | Composition [mol %] | 1-olefin | 11.1 | 1.8 | 1.5 | 2.3 |
| | | 2-olefin | 66.0 | 18.2 | 32.5 | 31.0 |
| | | 3-olefin | 18.1 | 16.2 | 22.5 | 24.2 |
| | | 4-olefin | 3.6 | 17.5 | 18.6 | 18.1 |
| | | 5-olefin | 0.6 | 15.4 | 11.8 | 10.6 |
| | | 6-olefin | 0.5 | 13.7 | 7.2 | 6.5 |
| | | 7-olefin | 0.0 | 8.6 | 3.0 | 3.5 |
| | | 8-olefin | 0.0 | 8.6 | 3.0 | 1.8 |
| | | 9-olefin | — | — | — | 1.8 |
| | | Total | 100.0 | 100.0 | 100.0 | 100.0 |
| | | $ADBP_1$ | 2.18 | 4.45 | 3.55 | 3.58 |
| Step 2 Composition after reaction | Composition [mol %] | 1-olefin | 9.6 | 1.5 | 1.3 | 1.9 |
| | | 2-olefin | 67.0 | 18.2 | 32.3 | 31.3 |
| | | 3-olefin | 18.6 | 16.1 | 22.4 | 24.0 |
| | | 4-olefin | 3.8 | 17.6 | 18.7 | 18.2 |
| | | 5-olefin | 0.7 | 15.5 | 11.9 | 10.8 |
| | | 6-olefin | 0.1 | 13.7 | 7.3 | 6.5 |
| | | 7-olefin | 0.1 | 8.7 | 3.0 | 3.3 |
| | | 8-olefin | 0.1 | 8.7 | 3.0 | 2.0 |
| | | 9-olefin | — | — | — | 2.0 |
| | | Total | 100.0 | 100.0 | 100.0 | 100.0 |
| | | $ADBP_2$ | 2.20 | 4.46 | 3.57 | 3.59 |
| | Δ(1-Ole) | | 1.5 | 0.3 | 0.2 | 0.4 |
| | ΔADBP | | 0.02 | 0.01 | 0.02 | 0.01 |

| | | | Example 9 | Example 10 | Comparative Example 1 |
|---|---|---|---|---|---|
| | Number of carbon atoms | | 16 | 16 | 16 |
| Step 1 Condition | Raw material olefin | | 1-hexadecene | 1-hexadecene | 1-hexadecene |
| | Catalyst | | γ-alumina | γ-alumina | zeolite |
| | Temperature | [° C.] | 280 | 280 | 150 |
| | Time | [hr or min] | — | — | 50 min |
| | LHSV | [$hr^{-1}$] | 2.9 | 2.9 | — |
| Step 2 Condition | Catalyst | | γ-alumina | γ-alumina | zeolite |
| | Catalyst amount | wt % or mL | 450 mL | 450 mL | 0.5 wt % |
| | Temperature | [° C.] | 160 | 160 | 175 |
| | Time | [hr or min] | — | — | 1 min |
| | LHSV | [$hr^{-1}$] | 0.09 | 0.55 | — |

TABLE 1-continued

| | | | | | |
|---|---|---|---|---|---|
| Step 1 Composition after reaction | Composition [mol %] | 1-olefin | 2.3 | 2.3 | 1.5 |
| | | 2-olefin | 22.4 | 22.4 | 32.5 |
| | | 3-olefin | 18.6 | 18.6 | 22.6 |
| | | 4-olefin | 18.3 | 18.3 | 18.5 |
| | | 5-olefin | 14.2 | 14.2 | 11.8 |
| | | 6-olefin | 11.2 | 11.2 | 7.2 |
| | | 7-olefin | 6.5 | 6.5 | 2.9 |
| | | 8-olefin | 6.5 | 6.5 | 2.9 |
| | | 9-olefin | — | — | — |
| | | Total | 100.0 | 100.0 | 100.0 |
| | | $ADBP_1$ | 4.12 | 4.12 | 3.55 |
| Step 2 Composition after reaction | Composition [mol %] | 1-olefin | 1.5 | 1.8 | 1.6 |
| | | 2-olefin | 22.7 | 22.6 | 31.6 |
| | | 3-olefin | 18.5 | 18.5 | 22.0 |
| | | 4-olefin | 18.4 | 18.4 | 18.5 |
| | | 5-olefin | 14.3 | 14.3 | 12.1 |
| | | 6-olefin | 11.4 | 11.3 | 7.6 |
| | | 7-olefin | 6.6 | 6.6 | 3.3 |
| | | 8-olefin | 6.6 | 6.6 | 3.3 |
| | | 9-olefin | — | — | — |
| | | Total | 100.0 | 100.0 | 100.0 |
| | | $ADBP_2$ | 4.15 | 4.14 | 3.60 |
| | Δ(1-Ole) | | 0.8 | 0.5 | −0.1 |
| | ΔADBP | | 0.03 | 0.02 | 0.05 |

According to the results of the examples of the present invention, the method of producing an internal olefin of the present invention provides a method of producing an internal olefin having a decreased 1-olefin content while preventing the double bond distribution of the internal olefin from being changed.

INDUSTRIAL APPLICABILITY

The present invention provides a method of producing an internal olefin having a decreased 1-olefin content while preventing the double bond distribution of the internal olefin from being changed. The internal olefin obtained by the method of producing an internal olefin of the present invention is useful as a raw material or an intermediate raw material of a surfactant, an organic solvent, a fabric softener, a sizing agent, and the like, and is useful as a raw material of a surfactant.

The invention claimed is:

1. A method of producing an internal olefin, comprising a step 1 and a step 2 in this order:

step 1: a step of isomerizing a raw material olefin having 8 or more and 36 or less carbon atoms to provide a mixture containing an internal olefin and a 1-olefin; and step 2: a step of isomerizing the 1-olefin contained in the mixture provided in the step 1 at a temperature that is lower than a reaction temperature in the step 1;

wherein an average double bond position of the internal olefin after completing an isomerization reaction in the step 1 is more inner than an average double bond position of the raw material olefin.

2. The method of producing an internal olefin according to claim 1, wherein the reaction temperature in the step 1 is 100° C. or more and 300° C. or less.

3. The method of producing an internal olefin according to claim 1, wherein the reaction temperature in the step 2 is a temperature that is lower than the reaction temperature in the step 1 by 30° C. or more.

4. The method of producing an internal olefin according to claim 1, wherein the raw material olefin contains a 1-olefin.

5. The method of producing an internal olefin according to claim 1, wherein the 1-olefin is a linear 1-olefin.

6. The method of producing an internal olefin according to claim 1, wherein the step 1 and the step 2 each are performed in the presence of a catalyst.

7. The method of producing an internal olefin according to claim 6, wherein the catalyst is a solid catalyst.

8. The method of producing an internal olefin according to claim 6, wherein the catalyst is a solid acid catalyst.

9. The method of producing an internal olefin according to claim 1, wherein an absolute value of a difference between an average double bond position of the internal olefin obtained in the step 1 and an average double bond position of the internal olefin obtained in the step 2 is 0.1 or less.

10. The method of producing an internal olefin according to claim 1, wherein an average double bond position of the internal olefin after completing the reaction in the step 1 is 1.5 or more.

11. The method of producing an internal olefin according to claim 1, wherein a content of the 1-olefin in the mixture obtained in the step 1 is 20 parts by mol or less per 100 parts by mol in total of the 1-olefin and the internal olefin.

12. The method of producing an internal olefin according to claim 1, wherein a reaction mode of the isomerization of the step 2 is a batch mode, and a reaction time in the step 2 is 0.05 hr or more and 60 hr or less.

13. The method of producing an internal olefin according to claim 1, wherein a reaction mode of the isomerization of the step 2 is a continuous mode, and an LHSV (liquid hourly space velocity) in the reaction of the step 2 is 0.05 $hr^{-1}$ or more and 5.0 $hr^{-1}$ or less.

14. The method of producing an internal olefin according to claim 1, wherein a decrement value from a content (% by mol) of the 1-olefin in the mixture obtained in the step 1 to a content (% by mol) of the 1-olefin obtained in the step 2 is 0.1% by mol or more.

15. A method of producing an internal olefin sulfonate salt, comprising sulfonating an internal olefin produced by the method of producing an internal olefin according to claim 1.

16. The method of producing an internal olefin according to claim 1, wherein a content of the 1-olefin in the mixture obtained in the step 1 is 1.0 parts by mol or more per 100 parts by mol in total of the 1-olefin and the internal olefin.

* * * * *